United States Patent
Gruhler et al.

(10) Patent No.: US 7,479,256 B1
(45) Date of Patent: Jan. 20, 2009

(54) METHOD AND DEVICE FOR APPLYING A PLURALITY OF MICRODROPLETS ONTO A SUBSTRATE

(75) Inventors: Holger Gruhler, Tuningen (DE); Nicolaus Hey, Eschbronn-Mariazell (DE); Hermann Sandmaier, Obereschach (DE); Roland Zengerle, Weiherstrasse 15/2, D-78050 Villingen-Schwenningen (DE)

(73) Assignees: Hahn-Schickard-Gesellschaft Fuer Angewandte Forschung E.V., Villingen-Schwenningen (DE); Roland Zengerle, Villingen-Schwenningen (DE)

( * ) Notice: Subject to any disclaimer, the term of this patent is extended or adjusted under 35 U.S.C. 154(b) by 0 days.

(21) Appl. No.: 10/069,852

(22) PCT Filed: Apr. 10, 2000

(86) PCT No.: PCT/EP00/03173

§ 371 (c)(1),
(2), (4) Date: May 22, 2000

(87) PCT Pub. No.: WO01/17669

PCT Pub. Date: Mar. 15, 2001

(30) Foreign Application Priority Data

Sep. 2, 1999 (DE) ................... 199 41 871

(51) Int. Cl.
*B01L 3/02* (2006.01)
(52) U.S. Cl. .................. 422/100; 347/21; 347/40; 347/47; 347/85; 347/97
(58) Field of Classification Search ............. 422/100; 374/17, 18, 21, 40–42, 47, 84–87, 97
See application file for complete search history.

(56) References Cited

U.S. PATENT DOCUMENTS

| | | | |
|---|---|---|---|
| 5,343,909 A | * | 9/1994 | Goodman |
| 5,508,200 A | | 4/1996 | Tiffany et al. |
| 5,551,487 A | | 9/1996 | Gordon et al. |
| 5,681,484 A | | 10/1997 | Zanzucchi et al. |
| 5,682,190 A | * | 10/1997 | Hirosawa et al. ............. 347/94 |
| 5,847,105 A | | 12/1998 | Baldeschwieler et al. |
| 6,024,925 A | * | 2/2000 | Little et al. ................. 422/100 |

(Continued)

FOREIGN PATENT DOCUMENTS

DE          3123796 A1          3/1982

(Continued)

*Primary Examiner*—Jan M Ludlow
(74) *Attorney, Agent, or Firm*—Michael A. Glenn; Glenn Patent Group

(57) ABSTRACT

A device for device for applying a plurality of microdroplets onto a substrate has a plurality of nozzle orifices in a dosing head. In addition to walls for defining a liquid column of a medium to be dosed on each nozzle orifice, a pressure chamber is provided, which is adapted to be filled with a buffer medium and which is arranged in such a way that said buffer medium can simultaneously be used for applying a pressure to the liquid-column ends which are spaced apart from the nozzle orifices. A pressure generator is provided for applying a pressure to said buffer medium in such a way that a plurality of microdroplets will simultaneously be applied onto the substrate through said plurality of nozzle orifices. Finally, liquid reservoirs for the media to be dosed, which are in fluid communication with the liquid columns on the nozzle orifices are provided.

19 Claims, 10 Drawing Sheets

U.S. PATENT DOCUMENTS 6,399,396 B1   6/2002  Bass
6,485,690 B1 * 11/2002 Pfost et al. .................. 422/102
6,855,293 B1   2/2005  Zengerle et al.

FOREIGN PATENT DOCUMENTS

| | | |
|---|---|---|
| DE | 19802368 C1 | 8/1999 |
| JP | 52 110484 | 9/1977 |
| JP | 59-178363 | 10/1984 |
| JP | 07 290705 | 11/1995 |
| JP | 08 219956 | 8/1996 |
| JP | 09 76513 | 3/1997 |
| WO | WO 97/45730 A1 | 12/1997 |
| WO | WO 98/51999 A1 | 11/1998 |
| WO | WO 00/56442 | 9/2000 |
| WO | WO 00/62932 A2 | 10/2000 |

* cited by examiner ns of the substrate and of the nozzles. The method described here is suitable for use in cases where the number of analytes does not exceed a few hundred per substrate.

METHOD AND DEVICE FOR APPLYING A PLURALITY OF MICRODROPLETS ONTO A SUBSTRATE

BACKGROUND OF THE INVENTION

1. Field of the Invention

The present invention relates to a device and a method for applying a plurality of microdroplets onto a substrate and in particular to such a device and such a method which permit the simultaneous application of a plurality of microdroplets. The present invention specially refers to such devices and methods which are suitable for producing so-called biochips in the case of which a plurality of different analytes is applied to a substrate so as to detect different substances in an unknown sample.

The fact that the genomes of human beings, animals and plants are deciphered to an increasing extent provides a large number of new possibilities ranging from the diagnosis of genetically conditioned diseases to a much faster search for pharmaceutically interesting agents. The above-mentioned biochips will, for example, be used in the future for examining food with respect to a large number of possible, genetically modified components. In another field of use, such biochips can be used for determining the exact genetic defect in the case of genetically conditioned diseases so as to derive therefrom the ideal strategy for treating the disease.

The biochips which are suitable for such cases of use normally consist of a carrier material, i.e. a substrate, having applied thereto a large number of different substances in the form of a raster. Typical raster distances in the array are distances between 100 µm and 1,000 µm. Depending on the respective case of use, the large number of different substances on a biochip, which are referred to as so-called analytes, ranges from a few different substances to a few 100,000 different substances per substrate. Each of these different analytes can be used for detecting a very specific substance in an unknown sample.

When an unknown sample fluid is applied to a biochip, reactions will occur in the case of specific analytes; these reactions can be detected with the aid of suitable methods, e.g. fluorescence detection. The number of different analytes on the biochip corresponds to the number of different components in the unknown sample fluid which can simultaneously by analyzed by the respective biochip. Such a biochip is a diagnostic tool with the aid of which an unknown sample can be examined with regard to a large number of constituents simultaneously and purposefully.

2. Description of Prior Art

For applying the analytes to a substrate in order to produce such a biochip, three fundamentally different methods are known for the time being. Depending on the number of biochips required and on the necessary number of analytes per chip, these methods are used alternatively.

The first method is referred to as "contact printing", a bundle of steel capillaries filled with various analytes in the interior thereof being used for executing this method. This bundle of steel capillaries is stamped onto the substrate.

When the bundle is taken off, the analytes adhere to the substrate in the form of microdroplets. In the case of this method, the quality of the printed pattern is, however, strongly determined by the effect of capillary forces and depends therefore on a large number of critical parameters, e.g. the quality and the coating of the surface of the substrate, the exact geometry of the nozzle and, primarily, the media used. In addition, the method is very susceptible to contaminations of the substrate and of the nozzles. The method described here is suitable for use in cases where the number of analytes does not exceed a few hundred per substrate.

In a second method for producing biochips, the so-called "spotting", so-called microdispensers are normally used, which, similar to an ink-jet printer, are capable of shooting individual microdroplets of a liquid onto a substrate in response to a respective control command. Such a method is referred to as "drop-on-demand". Microdispensers of this kind are commercially available from some firms. The advantage of this method is to be seen in the fact that the analytes can be applied onto a substrate in a contactless manner, the influence of capillary forces being then irrelevant. An essential problem is, however, that it is very expensive and extremely difficult to arrange a large number of nozzles, which are each supplied with a different medium, in parallel or rather in an array. The limiting elements are here the actorics and the media logistics, which cannot be miniaturized to the extent desired.

A third method which is used at present for producing biochips is the so-called "synthesis method" in the case of which the analytes, which normally consist of a chain of linked nucleic acids, are chemically produced on the substrate, i.e. synthesized. For delimiting the spatial positions of the various analytes, methods are used which are known from the field of microelectronics, e.g. lithographic methods with masking techniques. This synthesis method is by far the most expensive one among the above-mentioned methods, but it can also be used for producing the greatest variety of analytes on a chip, in the order of magnitude of 100,000 different analytes per substrate.

SUMMARY OF THE INVENTION

It is the object of the present invention to provide devices for applying a plurality of microdroplets onto a substrate, which permit microdroplets to be applied to a substrate simultaneously, in a regular pattern, at a reasonable price and exactly, as well as a method for use in the production of such a device.

According to a first aspect of the invention, this object is achieved by a device for applying a plurality of microdroplets onto a substrate, comprising:

a plurality of nozzle orifices in a dosing head;

walls for defining a liquid column of a medium to be dosed on each nozzle orifice;

a pressure chamber which is adapted to be filled with a buffer medium and which is arranged in such a way that said buffer medium can simultaneously be used for applying a pressure to the liquid-column ends which are spaced apart from the nozzle orifices;

a pressure generator for applying a pressure to said buffer medium in such a way that a plurality of microdroplets will simultaneously be applied onto the substrate through said plurality of nozzle orifices; and liquid reservoirs for the media to be dosed, which are in fluid communication with the liquid columns on the nozzle orifices.

According to a second aspect of the invention, this object is achieved by a dosing head for a device for applying a plurality of microdroplets onto a substrate, said device comprising:

a plurality of nozzle orifices in a dosing head;

walls for defining a liquid column of a medium to be dosed on each nozzle orifice;

a pressure chamber which is adapted to be filled with a buffer medium and which is arranged in such a way that said buffer medium can simultaneously be used for applying a pressure to the liquid-column ends which are spaced apart from the nozzle orifices;

a pressure generator for applying a pressure to said buffer medium in such a way that a plurality of microdroplets will simultaneously be applied onto the substrate through said plurality of nozzle orifices; and liquid reservoirs for the media to be dosed, which are in fluid communication with the liquid columns on the nozzle orifices;

said dosing head comprising a substrate having the plurality of nozzle orifices in a first surface thereof, having a plurality of liquid reservoirs in a surface thereof which is located opposite to said first surface, and having fluid lines which connect respective nozzle orifices to respective liquid reservoirs and at least part of which is defined by open trenches formed in said first or second surface, said trenches having depth and width dimensions of such a nature that a liquid will be retained therein by a capillary effect alone.

The present invention is based on the finding that it is possible to apply a plurality of microdroplets simultaneously onto a substrate by applying to liquid columns positioned on nozzle orifices simultaneously a pressure via a common buffer medium. The buffer medium is preferably inert in that a short pressure pulse applied via this buffer medium will homogeneously be advanced to the liquid columns of all the nozzles, and that, in addition, a mixing of different media applied to the nozzle orifices will be prevented, i.e. the buffer medium has dosing media-separating properties.

According to the present invention, the nozzle orifices and the nozzles, respectively, can be arranged such that they are spaced from one another at the same distance at which also the fluid droplets are to be applied to the substrate. If the nozzles are to be arranged very close to one another, each nozzle is preferably connected through a separate media line to a larger, outwardly arranged reservoir through which each nozzle and each nozzle orifice can be supplied with a specific liquid. If the distances between the nozzles are, however, large enough for supplying the nozzles with liquid by means of conventional methods, e.g. by means of standard automatic pipetting devices, the media lines and the liquid reservoirs can be dispensed with; the liquid reservoir can then be arranged directly above the nozzle.

In order to apply a pressure pulse to the buffer medium according to the present invention, a diaphragm having an actor associated therewith is used in preferred embodiments of the present invention. However, the pressure pulse can also be produced in any other imaginable way, e.g. by producing by means of a chemical or thermal event an excess pressure in the pressure chamber in which the buffer medium is contained. A tappet with an associated actor can, for example, be used. Furthermore, the pressure generating means may comprise a compressed-air supply means which is in fluid communication with the pressure chamber.

According to the present invention, the fast pressure pulse produced acts homogeneously onto all nozzles and accelerates the liquid contained in these nozzles. Hence, microdroplets can be ejected from a plurality of nozzle orifices simultaneously. In addition, the buffer medium according to the present invention prevents a mixing of different media, when different media to be dosed are applied to a substrate.

According to the present invention, the liquid column on the nozzle orifices is preferably produced in that the nozzle orifice is the outer end of a channel which is adapted to be filled by a capillary effect, the liquid column being defined in said channel. This channel is then preferably connected to a liquid reservoir via the fluid connection line in such a way that capillary filling of the channel can always be realized.

According to a third aspect of the invention, the above object is achieved by a method of producing a through-hole having a defined cross-sectional area in the substrate of a dosing head, said method comprising the steps of:

producing a first elongate trench structure of defined width and depth in a first surface of the substrate;

producing a second elongate trench structure of defined width and depth in a second surface of the substrate which is located opposite to said first surface, in such a way that said first and second trench structures intersect so that an opening having a defined cross-sectional area is formed in the area of intersection.

It follows that the present invention provides by means of which microdroplets, in particular microdroplets of biologically relevant substances, can be produced and applied onto a substrate in a regular pattern. Furthermore, the present invention provides a dosing head for such a device for applying a plurality of microdroplets onto a substrate and a method that can advantageously be used in the production of such a dosing head.

Further developments of the present invention are disclosed in the dependent claims.

BRIEF DESCRIPTION OF THE DRAWINGS

In the following, preferred embodiments of the present invention will be explained in detail making reference to the drawings enclosed, in which.

DESCRIPTION OF PREFERRED
EMBODIMENTS OF THE INVENTION

Figure 1:
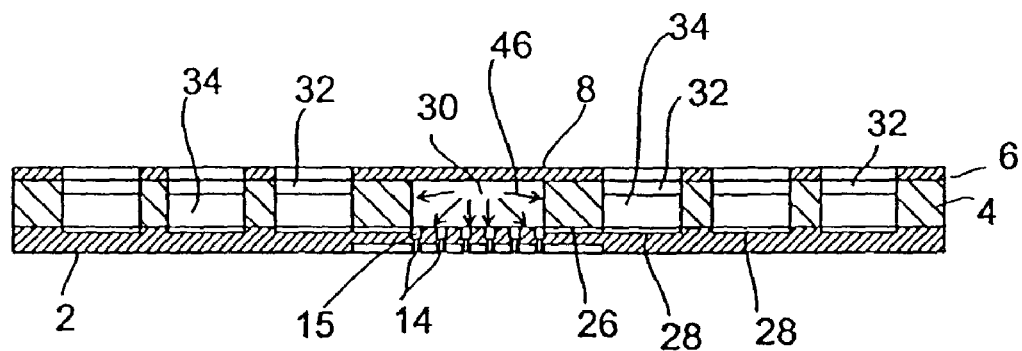
FIG. 1 shows schematically a cross-sectional view of an embodiment of a device according to the present invention.

As can be seen in FIG. 1, the depicted embodiment of a device for applying a plurality of microdroplets onto a substrate consists of a patterned silicon substrate 2, an intermediate plate 4 applied to the silicon substrate 2 and a layer 6 which is applied to the intermediate plate 4 and which has formed therein a pressure generating device in the form of a displacement diaphragm 8.

Figure 2:
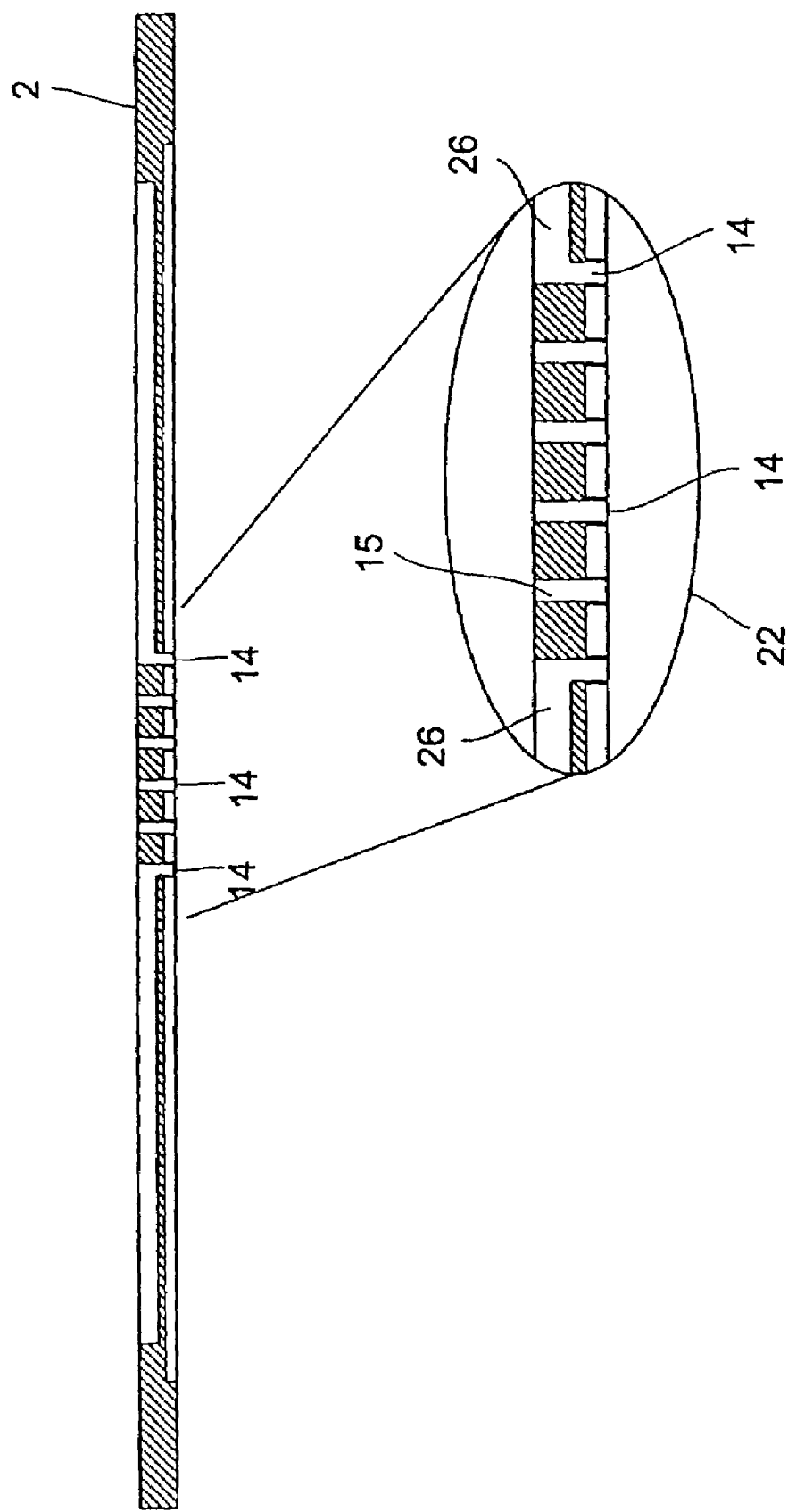
FIG. 2 shows schematically a cross-sectional view of a silicon substrate used in the device according to FIG. 1.
Figure 3:
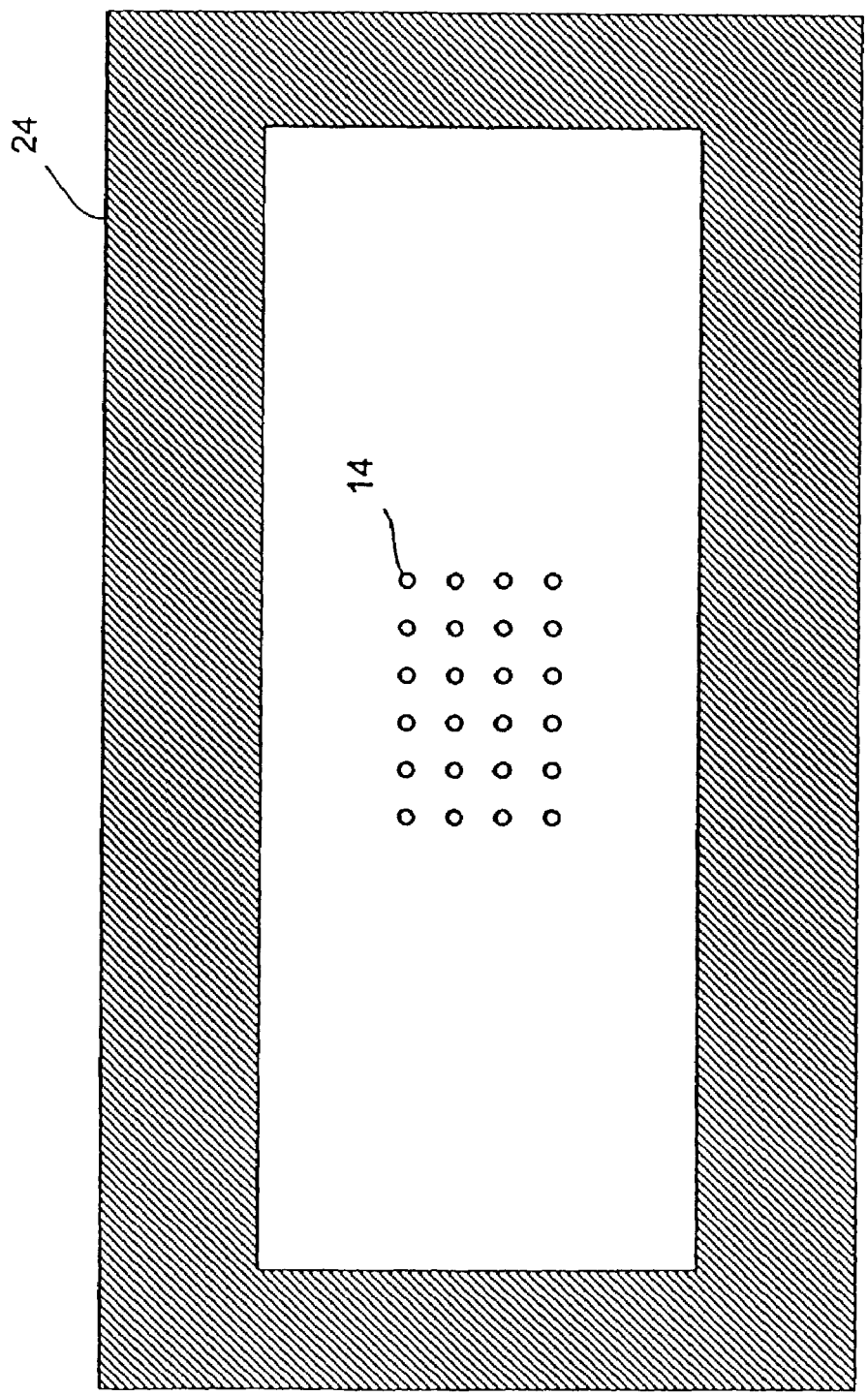
FIG. 3 shows schematically a bottom view of the substrate shown in FIG. 2.

To begin with, the structural design of the silicon substrate 2 will be explained in detail especially with respect to FIGS. 2-4, which each show enlarged views of this silicon substrate 2. As can be seen, a plurality of nozzles having lower nozzle orifices 14 are formed in a lower surface of the silicon substrate 2. The nozzles are preferably of such a size that capillary filling thereof is possible, and, in addition, they are micropatterned in the lower surface of the chip 2 in such a way that they are exposed relative to the surrounding silicon surface. In the figures, six juxtaposed nozzles are shown, a bottom view of the silicon chip 2 with the nozzle orifices 14 structured in the lower surface thereof being shown in FIG. 3, where it can be seen that the embodiment shown comprises twenty-four nozzles. As can also be seen, the nozzles are exposed relative to the surrounding silicon surface, the surround 24 constituting the outer edge of the silicon chip 2. In this connection, it should be pointed out that the surround in the representation of FIG. 3 is reduced in width in comparison with the representation of FIG. 1.

Above the nozzle orifices 14 of the nozzles, respective channels 15 are arranged through which a liquid column can be defined on top of the nozzle orifice 14 in question. The respective nozzles are connected to media reservoirs 28, which are formed in the surface of the silicon chip 2, via media lines 26 which can, in particular, be seen in FIG. 4 and in the enlarged section 22 in FIG. 2. In this connection, it should be pointed out that only two media lines 26 can be seen in the cross-sectional views of FIGS. 1 and 2. As can be seen in FIG. 4, twenty-four media reservoirs 28 are connected via media lines 26 to the respective nozzles of the silicon chip 2.

In the embodiment shown, the media reservoirs 28 are patterned in the silicon-chip surface located opposite the nozzle orifices 14. The media reservoirs 28 are preferably implemented such that they can automatically be filled with liquids by means of standard automatic pipetting devices. For this purpose, these media reservoirs may e.g. have identical diameters and they may be arranged at identical distances from one another like the chambers of a known 348-well microtitre plate. The media lines 26 are preferably implemented such that liquids are drawn from the media reservoirs 28 via the media lines through capillary forces to the nozzle orifices 14. The channels 15 of the closely spaced nozzle orifices 14 can in this way be supplied via the media lines 26 with liquid from larger reservoirs 28. Hence, a format conversion takes place between the media reservoirs 28 and the nozzle orifices 14.

The nozzle orifices 14 shown may have a diameter of e.g. 200 μm, and also the media lines may have a width of 200 μm. The depicted array of twenty-four nozzles can therefore easily be arranged at a mutual distance of 1 mm. The limiting factor for the number of nozzles which can be arranged in an array is the width of the connecting channels which interconnect the nozzles and the media reservoirs. These connecting channels must be conducted to the outside between the nozzles. If the width of these channels is reduced still further, it will also be possible to accommodate 48, 96 or an even higher number of nozzles on a dosing head.

In the depicted embodiment of the present invention, an intermediate plate 4 is arranged on the silicon chip 2; this intermediate plate 4 is provided with a recess 30 which is arranged above the nozzles so that this recess 30 can serve as a pressure chamber 30 for accommodating a buffer medium. The buffer medium arranged in the pressure chamber 30 is preferably a gas mixture or an air mixture.

In the embodiment shown, the intermediate plate 4 is additionally provided with recesses 32 causing an increase in the capacity of the media reservoirs 28 formed in the silicon chip 2, so that a larger amount of liquid 34 can be accommodated.

In the embodiment shown, the diaphragm 8 is provided as a pressure generating device on top of the pressure chamber 30; by means of this diaphragm 8, an excess pressure can be produced in the pressure chamber 30. The diaphragm 8 can e.g. consist of an elastic foil or of silicon. In order to simplify the production, this diaphragm can be part of a layer 6 which is applied to the upper surface of the intermediate plate 4, the layer 6 being then preferably provided with openings in the area of the media reservoirs 28, 32 so that these media reservoirs can be refilled.

In order to produce an abrupt deflection of the displacement diaphragm 8, a mechanical device (not shown in FIG. 1) can preferably be provided; this mechanical device can be defined e.g. by a pneumatic piston which is arranged above the displacement diaphragm 8 as a modular component, without any fixed connection to the section of the device according to the present invention shown in FIG. 1. Alternatively, the actor may also comprise a piezoactor or a purely mechanical structure, e.g. a spring.

Figure 5:
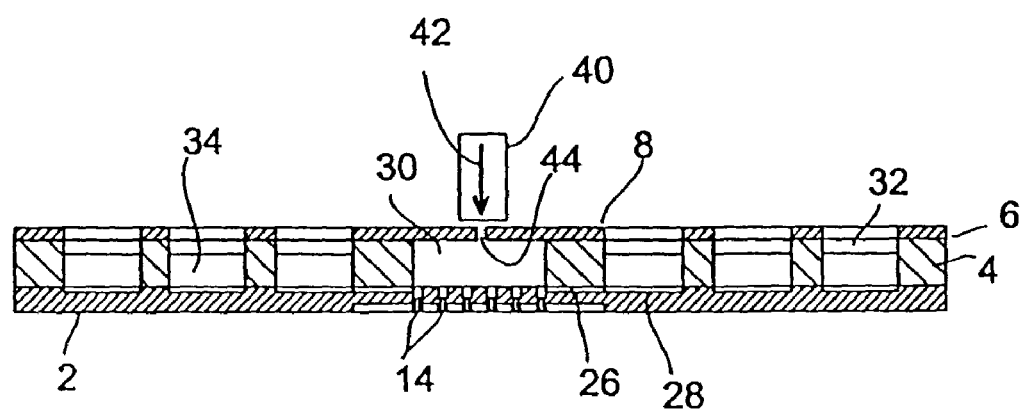
FIG. 5 shows a schematic cross-sectional view for explaining an alternative embodiment of a device according to the present invention.

Such an actor component is schematically shown in FIG. 5 and designated by reference numeral 40; this actor component 40 can cause a movement along the arrow 42 so as to generate a pressure in the pressure chamber 30. As can additionally be seen in FIG. 5, a vent valve 44 is arranged in the displacement diaphragm 8 in the embodiment shown, this vent valve being used for preventing the liquid volumes arranged in the nozzles from being accelerated in the direction of the displacement diaphragm 8 when the displacement diaphragm 8 relaxes. In the embodiment shown in FIG. 5, the vent valve 44 is shown as an active valve which is closed by the actor 40 itself, when the displacement diaphragm 8 is displaced so as to generate an excess pressure in the pressure chamber 30, whereas it is opened for venting during the return movement of the actor component 40. The actor speed is higher than the speed of the displacement diaphragm 8 produced by the relaxation of the diaphragm.

In the following, the mode of operation of the described device according to the present invention will be described. At first, the media reservoirs 28, 32 are preferably filled with different media which are to be applied onto a substrate; making use of e.g. a conventional microtitre plate, this filling can be effected with the aid of standard automatic pipetting devices, as has been explained hereinbefore. Due to the media-line and nozzle dimensions provided in the case of the preferred embodiment of the present invention, the nozzles are now automatically filled up to the lower nozzle orifices 14 by means of a capillary effect. The pressure chamber 30 has now arranged therein the buffer medium, e.g. an air mixture or a gas mixture; this mixture can consist of the ambient air or of a mixture which is specially introduced through the opening 42. In any case, the buffer medium has media-separating properties with respect to the liquids to be dosed so that the media to be dosed will not mix in the pressure chamber 30. In order to support this media-separating property, the upper surface of the chip can be covered with a hydrophobic layer. It can thus be guaranteed more reliably that liquids from different media lines will not be mixed in the area of the nozzles. In addition, also the lower surface of the chips in which the nozzle orifices are formed may be covered with a hydrophobic layer.

When the nozzles have been filled, preferably by capillary effects, up to their orifices with the liquid to be dosed, a pressure pulse is caused by the actor 40 so as to generate in the pressure chamber 30 a mechanical displacement by the displacement diaphragm 8. This will have the effect that a homogeneous pressure pulse will propagate in the pressure chamber 30 through the buffer medium, as shown by the arrows 46 in FIG. 1. The fast pressure pulse produced acts homogeneously on all nozzles and accelerates the liquid columns at the nozzle orifices 14. The liquid in the media lines 26, which represents a fluidic parallel circuit to the channels 15 in which the liquid columns are arranged, is, due to the higher flow resistance, accelerated far less strongly than the volume of the liquid columns applied to the nozzle orifices. The liquid is therefore ejected through all nozzle orifices 14 simultaneously. This ejection is caused by the circumstance that the buffer medium compressed by the displacement movement produces an excess pressure in the pressure chamber 30 due to the expansion tendency thereof. If the nozzles are empty or if the excess pressure of the buffer medium has been reduced to such an extent that liquid will no longer detach itself from the nozzles, the nozzles will refill due to the capillary forces acting in the media lines 26.

Following this, the displacement diaphragm 8 is returned to its original position by operating the actor component 40 accordingly. In order to avoid a negative pressure, which would be generated by the relaxation of the displacement diaphragm, in the pressure chamber 30, the vent valve 44 is provided. This vent valve permits the pressure chamber to be vented at the moment of diaphragm relaxation so that the liquid arranged in the nozzles will not be accelerated in the direction of the displacement diaphragm 8. When the displacement diaphragm 8 has returned to its starting position, the next dosing operation can be carried out.

Alternatively to the above-described active vent valve 44, also a passive valve can be provided, which may e.g. be a very small vent hole that may be provided at an arbitrary position of the pressure chamber 30. This vent hole can preferably be arranged in the displacement diaphragm as well as on the side of the nozzle in silicon. In the case of fast diaphragm movements of the type carried out e.g. for ejecting the plurality of microdroplets, this vent hole does not permit pressure compensation, but if the diaphragm relaxes comparatively slowly, it will permit pressure compensation thus preventing a negative pressure in the pressure chamber so that a disadvantageous pressure difference at the nozzles can be avoided.

In the above description, the expression nozzle 14 has been used for defining an outwardly directed nozzle orifice and a means arranged on top of this nozzle orifice for defining a liquid column on this nozzle orifice. For ejecting a microdroplet, the buffer medium applies pressure to the liquid-column which is spaced apart from the nozzle orifice. In order to increase the liquid volume in the nozzle, i.e. the liquid volume of the liquid column, an open standpipe can be arranged axially on top of the nozzle orifice in addition to the channels provided. These standpipes can be connected to the media lines via a T-shaped connection close to the nozzle, the media lines interconnecting the nozzles to the respective media reservoirs as before. The standpipes fill with liquid from the media lines due to capillary forces alone. In this case, the buffer medium will apply pressure to the standpipe end which is spaced apart from the nozzles.

If the standpipes or also the nozzle area can directly be filled with liquid by means of conventional methods, e.g. by automatic pipetting devices or by microdispensers or the like, the connected reservoirs and the media lines can be dispensed with. Otherwise, the outwardly arranged reservoirs, which can be seen in the top view of FIG. 4, represent a preferred embodiment, since they can easily be filled by standard automatic pipetting devices and since, by means of these reservoirs, possibly provided standpipes can be caused to fill automatically through capillary forces.

Preferably, the device for applying a plurality of microdroplets onto a substrate according to the present invention can be used for applying a different liquid medium onto the substrate by means of each nozzle. It is, however, also imaginable that a plurality of nozzles define a group of nozzles which has then supplied thereto the same liquid via a common media line.

Figure 4:
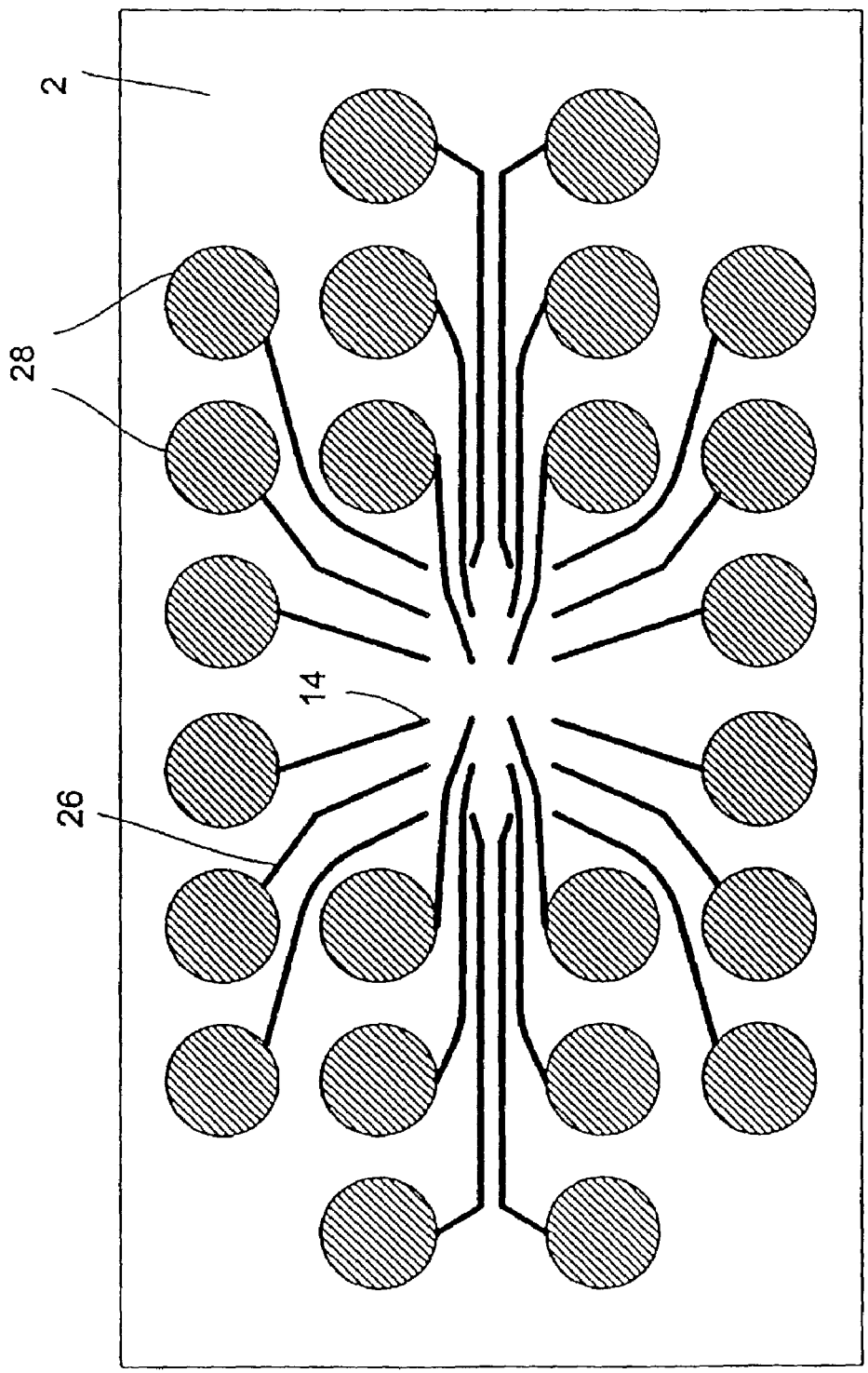
FIG. 4 shows a top view of the substrate shown in FIG. 2.

The media lines 26 shown in FIG. 4 are formed side by side in the surface of the silicon chip 2. As has been mentioned hereinbefore, this arrangement of the media lines restricts the packing density of the nozzles. In order to be able to increase the packing density of the nozzles, it is possible to mount a plurality of cover plates and/or intermediate plates one on top of the other and to distribute the media lines then in several planes. When lines are conducted in different planes, they can also seemingly intersect, without mixing of the liquids in the respective lines taking place. In this respect, it should be pointed out that in the area of the nozzles the media lines can be conducted as open lines and they can also be provided with a cover. Open media lines are advantageous insofar as they fill within a shorter period of time and are more resistant to contamination. Covered media lines are advantageous insofar as cross-contamination between different media lines can be reliably excluded.

As has already been mentioned hereinbefore, any pressure generating device which is able to apply a pressure pulse to the buffer medium can be used. Preferably, a displacement diaphragm is used for this purpose, this displacement diaphragm being driven by a suitable actor, e.g. a pneumatic piston, a piezoactor or a spring. Due to the compressibility of the gas, the necessary displacement path depends, on the on hand, on the size of the volume in which the buffer medium is arranged and, on the other hand, it depends on the size of the nozzles; the displacement path should be adjustable via a variable actuating path of the actor. When the displacement diaphragm is implemented as a conductive component, the actor can be caused to assume a defined reference position with respect to the diaphragm via the detection of an electric contact.

Making reference to FIG. 6, an alternative embodiment of a device according to the present invention with a deviating pressure generating device will be explained in the following. FIG. 6 shows again a dosing-head substrate 102; in the lower surface of this substrate 102, nozzle orifices 104 are formed, which are connected via fluid lines 106 with liquid reservoirs 108 formed in an intermediate layer 110. In the embodiment shown, the intermediate layer 110 has arranged thereon a cover plate 112 in which vent holes 114 for the fluid reservoirs 108 are formed.

Figure 6:
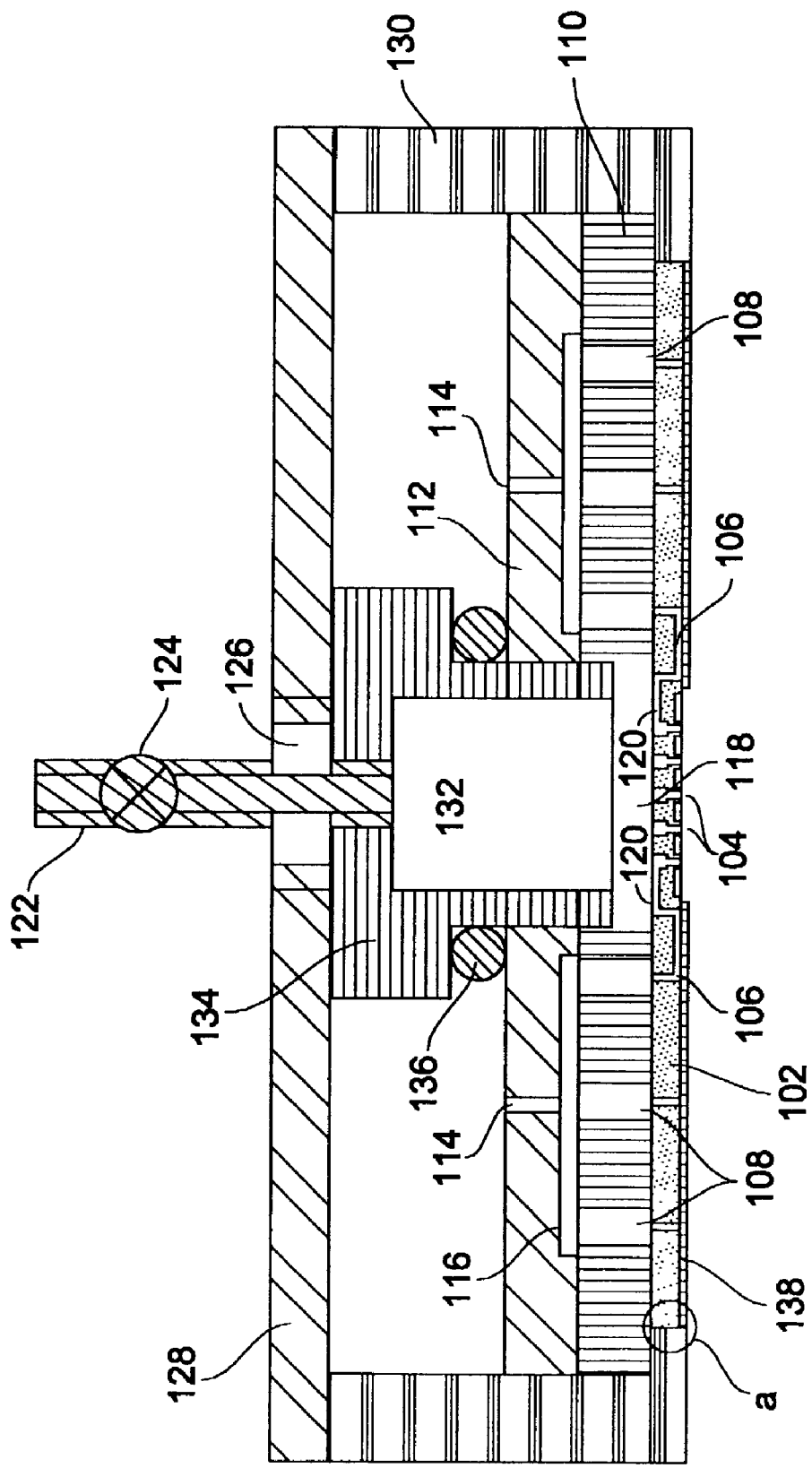
FIGS. 6, 7 and 8 show schematic cross-sectional views of further embodiments of devices according to the present invention.

As can be seen in FIG. 6, the cover plate 112 is provided with respective recesses 116 in such a way that a respective vent hole 114 is provided for a plurality of fluid reservoirs. In view of the fact that these vent holes are provided, no negative pressure will build up in the liquid reservoirs 108 during the capillary refilling flow of the media to be dosed. In order to additionally reduce the evaporation from the liquid reservoirs 108, the vent holes 114 preferably have a smaller cross-sectional area than the reservoir openings. As can be seen in FIG. 6, this can preferably be achieved in that a single vent hole 114 is provided for a plurality of liquid reservoirs 108. In order to reduce media evaporation still further, the cover plate 112 can additionally be implemented as a cooling means by making this cover plate preferably of a material having a good thermal conductivity, which is either mechanically connected to special cooling elements, e.g. Peltier elements, or which has supplied thereto a pre-cooled liquid through a structured pattern of channels. Alternatively, the vent holes 114 can also be provided in a wound or meandrous design so as to reduce the evaporation still further. In addition to the above-described effect of a reduced evaporation, the cover plate 112 also leads to a mechanical stabilization of the dosing head, since mechanical forces introduced by the actor will be absorbed by this cover plate.

As can be seen in FIG. 6, a recess, which defines a pressure chamber 118, is defined in the intermediate layer 110 above the nozzle orifices 104. The pressure chamber 118 has again arranged therein the buffer medium, which is air in the embodiment shown. At this point reference should be made to the fact that the fluid lines 106, which are open towards the pressure chamber 118 in the areas 120, are preferably implemented such that a liquid to be dosed is retained therein by capillary forces, whereas air is forced out of the fluid lines in this way.

In the embodiment shown in FIG. 6, the pressure generating means includes a compressed-air supply line 122, which is provided with a valve 124, so as to apply pressure to the buffer medium. The compressed-air supply line 122 of the embodiment shown is secured to a housing plate 128, which can be part of a holding device 130, with the aid of a fastening means 126, e.g. a screw joint. The compressed-air supply line 122 is provided with an area 132 of enlarged cross-section which ends in the pressure chamber 118. The area of enlarged cross-section is defined by an insert 134. The insert 134 is attached to the cover plate 112 by means of a seal 136, e.g. an O-ring, the housing plate 128 being preferably used as a pressure plate. By means of the area 132 having an enlarged cross-section, a defined pressure can be applied to the nozzle orifices 104 arranged at the opposite end of the pressure chamber. In other words, the pressure generating means comprises a supply line 122 communicating via an intermediate valve 124 with the liquid-column ends which are located in spaced relationship with the nozzle orifices 104. When the supply line 122 is under an output pressure up to the initially closed valve 124, opening of the valve will cause an inflow of buffer medium, which is air in the case of the preferred embodiment, and increase the pressure at the above-mentioned ends of the liquid columns. The increase in pressure ends when the valve 124 is closed. Depending on the switching time of the valve 124, either only a sub-volume of the liquid column or, maximally, the whole filling volumes of the columns are discharged through the nozzle orifices 104 onto a target substrate (not shown) in the course of this process. When the valve has been closed, pressure reduction can be temporally accelerated by opening an additional vent channel (not shown in FIG. 6).

In FIG. 6, a lower cover layer 138 is additionally shown, which is normally very thin so that the substrate onto which the microdroplets are to be applied can be positioned at the shortest possible distance from the plane of the nozzle orifices 104 during the dosing operation. The lower cover layer, which is provided with an opening in the area of the nozzle orifices 104, can be used for retaining the liquids in the fluid lines and, simultaneously, it will protect the nozzle orifices against contamination and destruction.

Figure 10:
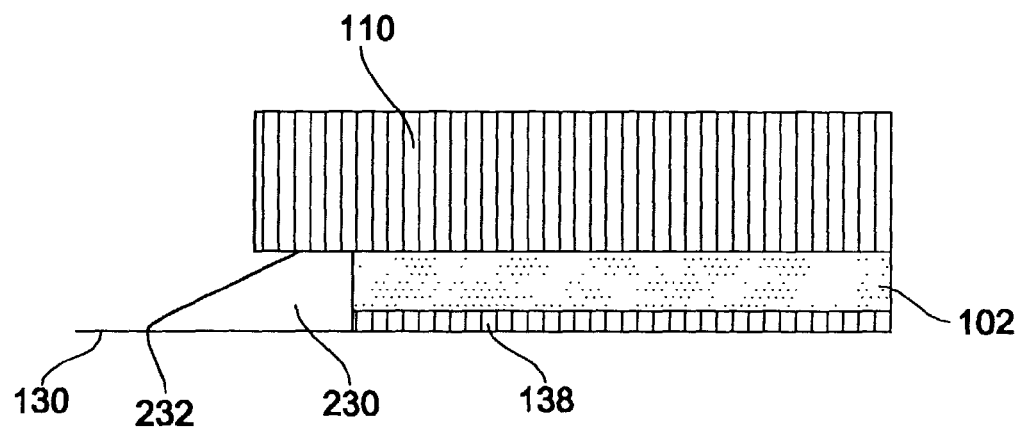
FIG. 10 shows a schematic, enlarged view of a section a in FIG. 6.

The way in which the holding device 130 is mounted will be explained in detail hereinbelow making reference to FIG. 10.

Figure 7:
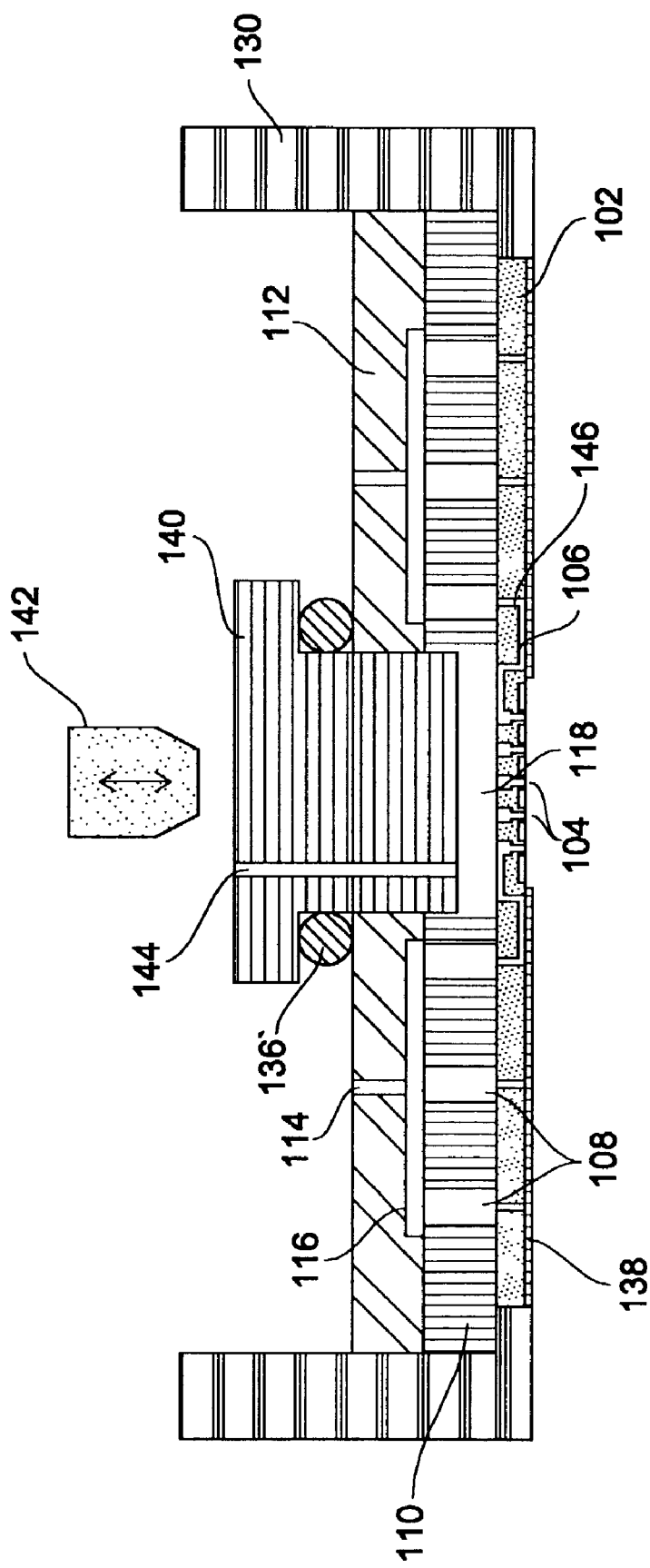

FIG. 7 shows a further embodiment of a device according to the present invention in the case of which an alternative pressure generating means is used. In FIG. 7 elements which are identical to those of FIG. 6 are designated by the same reference numerals and will not separately be described once more in the following.

In the embodiment shown in FIG. 7, the pressure generating means comprises a tappet 140 and an actor 142 which is operatively associated therewith. The tappet 140 is attached to the cover plate 112 via an elastic sealing ring 136'. The elastic sealing ring 136' serves to define a pressure chamber volume which is sealed from its surroundings and, when the tappet 140 is operated by the actor 142, it guarantees an upwardly closed pressure chamber volume of the pressure chamber 118. The tappet 140 can be fixed mechanically to the actor 142 or, as schematically shown in FIG. 7, it may have no fixed connection. In FIG. 7, a vent hole 144 is additionally shown, which is provided in the tappet 140; apart from the straight shape shown in FIG. 7, this vent hole 144 may have any shape which is suitable for venting the pressure chamber 118.

The tappet 140 can be pressed by means of the actor 142 in the direction of the nozzles 104 in a highly dynamic manner, whereby the volume of the pressure chamber 118 will be reduced so that the trapped buffer medium, which is air in the case of the preferred embodiment, will be compressed in the pressure chamber and the pressure will increase. This has the effect that microdroplets are ejected from the nozzle orifices 104. After the ejection of the microdroplets, the deflected tappet 140 is returned to its starting position by the resetting force of the elastic sealing means 136' alone.

The pressure generating means including a tappet 140, as shown in FIG. 7, has the advantage that, in spite of the fact that the capacity of the liquid reservoirs 108 has been enlarged by the intermediate plate 110, the volume of the pressure chamber 118 can be implemented such that it is very small. When the pressure chamber 118 contains a gaseous buffer medium, the compressible volume fraction can be reduced through the smaller chamber volume when pressure is built up. It follows that, on the basis of the same temporal deflection behaviour of the actor 142, an increased chamber pressure can be generated and the velocity of the droplets can be enhanced, consequently.

As can be seen in FIGS. 6 and 7, through-holes can be provided in the dosing-head substrate 102 so that the fluid lines 106 are conducted alternately on the upper side or on the lower side of the dosing-head substrate. One through-hole can also be arranged directly below the fluid reservoir, as has been indicated by reference numeral 146 in FIG. 7. It follows that the medium to be dosed can here be conducted on the lower side of the substrate.

Although the embodiments of the present invention described hereinbefore are embodiments in the case of which the nozzle orifices, the fluid lines, the fluid reservoirs and the means for defining a liquid column are each arranged in a specific way in a dosing-head substrate, preferably a silicon substrate, an intermediate plate or a cover plate, it will be obvious to those skilled in the art that the various functional elements can be arranged in the different layers in any realizable manner.

Figure 8:
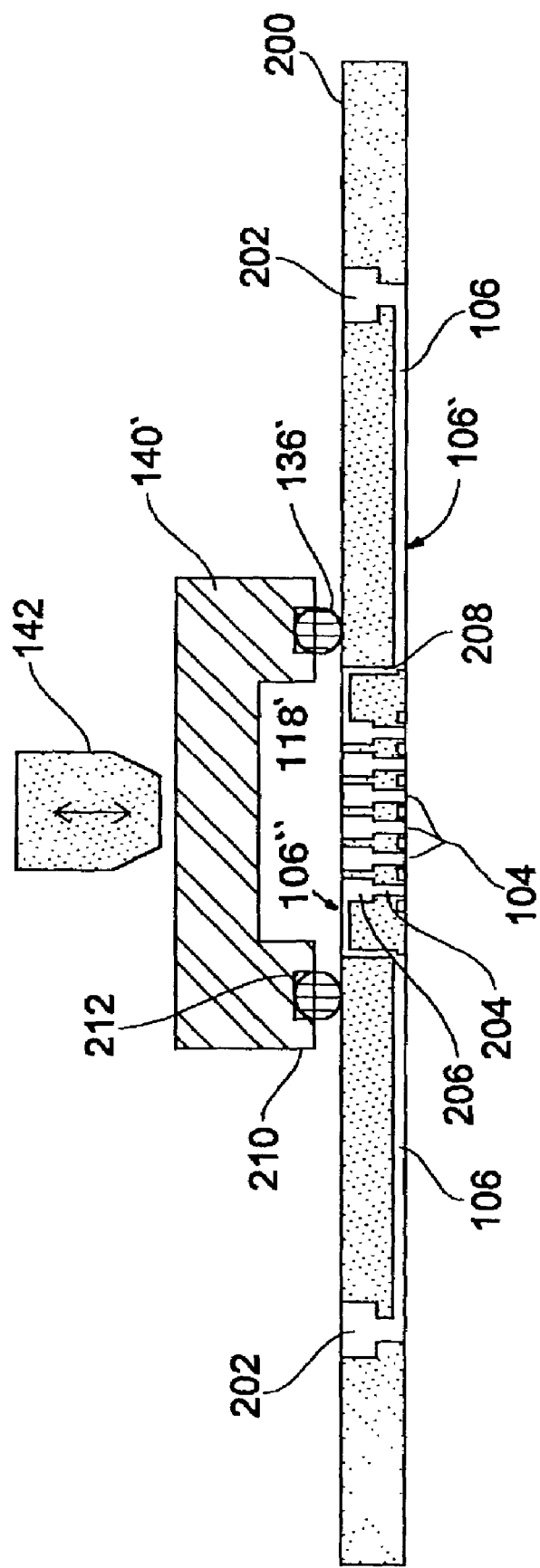

In FIG. 8, for example, an embodiment of the device according to the present invention is shown in the case of which the whole media logistics, i.e. the nozzle orifices, the fluid lines and the fluid reservoirs, are arranged in a single substrate 200 so that any kind of cover plate, the upper one as well as the lower one, can be dispensed with. In this case, the fluid channels 106 must have a capillary force which is so high that the liquids to be dosed are retained in these channels by this capillary force alone. These fluid lines 106 are, on the one hand, connected to fluid reservoirs 202 provided in the substrate 200 and, on the other hand, they are connected to nozzle orifices 104 which are arranged in this substrate 200.

In FIG. 8, just as in FIGS. 6 and 7, a respective nozzle channel 204 is arranged above the nozzle orifices 104, and a standpipe 206 is arranged on top of the nozzle channel; the nozzle channel 204 and the standpipe 206 define together the liquid column of a medium to be dosed at each nozzle orifice. Alternatively, it can again suffice to provide only the nozzle channel 204 as a means for defining a liquid column.

The fluid lines 106 and in particular the areas 106' and 106" thereof, which are formed in the lower and upper surfaces of the substrate 200, have depth and width dimensions of such a nature that a liquid contained therein will be retained therein by a capillary effect alone. A sufficient capillary effect of the fluid lines 106 can be realized by implementing these fluid lines such that they have a very small width and, in comparison with their width, a great depth.

In view of the fact that the fluid lines 106 are open towards the upper surface and the lower surface, respectively, it must, in the case of a substrate of the type shown in FIG. 8, be guaranteed that the flow resistance in the through-hole 208 exceeds the flow resistance of the nozzle orifices 104 to a sufficient extent so as to guarantee that, by means of the pressure generating means, microdroplets will only be ejected through the nozzle orifices, but neither through the through-hole 208 nor via the fluid lines 106. It follows that a very low flow resistance must be realized in the through-hole 208 with a very high production precision. An embodiment showing how a through-hole 208 can be produced with very high precision will be described in detail hereinbelow making reference to FIG. 12.

The pressure generating means shown in FIG. 8 comprises again a tappet 140' and an actor 142 associated therewith, the tappet 140' being operatively connected to the substrate 200 via an elastic sealing ring 136'. In the embodiment shown in FIG. 8, most of the pressure chamber 118' is defined by a recess in the tappet 140'. In the boundary area 210 which surrounds the recess defining the pressure chamber 118', the tappet 140' is provided with a circumferentially extending groove 212 in which the elastic sealing ring 136' is arranged or preferably secured in position. A force can now be applied to the tappet 140' via the actor 142 so that, by a compression of the elastic sealing ring 136', an excess pressure can be generated in the pressure chamber 118'; this excess pressure causes an ejection of microdroplets through the nozzle orifices 104. It should here be pointed out that the pressure chamber 118' need not be fully defined by a recess in the tappet 140', but that optionally or simultaneously the substrate 200 can additionally be structured so as to contribute to the formation of the pressure chamber.

In the embodiment shown in FIG. 8, the pressure generating means and the substrate 200 can be implemented as separate elements which are adapted to be separated completely from one another, since the sealing ring 136' need not be connected to the substrate. Hence, a plurality of carrier substrates can be supplied one after the other in one production series and microdroplets can therefore be applied onto a plurality of carrier substrates. This applies in the same way to the embodiment shown in FIG. 7, since a fixed connection between the pressure generating means and the dosing head need not exist in the case of this embodiment either.

The dosing-head substrate 200 shown in FIG. 8 can be produced by conventional micropatterning in silicon, the arrangement being, however, also particularly suitable for implementation in plastic materials, e.g. a production by means of an embossing technique. Since the fluid lines are highly capillary and open towards one side, any instantaneously existing air inclusion will, in addition, be forced out of the channel. Furthermore, the open channels offer a possibility of directly accessing the substrate for the purpose of cleaning.

As has already been mentioned, the pressure chamber can either be structured into the substrate, at least partially, and/or it can be formed fully or partly in the head of the associated actor, as has been described in connection with the tappet 140' making reference to FIG. 8. In the case of this embodiment, which is not provided with any cover plates, it is necessary that the substrate through-holes of the fluid lines and channels, respectively, have a markedly larger flow resistance than the nozzles channels so that, when the pressure pulse is being triggered, microdroplets will be discharged only by the nozzle orifices. This can easily be achieved by providing the substrate through-holes with an opening width whose cross-section is markedly smaller than that of the nozzle orifice. In the embodiment according to FIG. 8 cover plates can therefore be dispensed with completely, a decisive advantage of this embodiment being that air inclusions which may perhaps occur during the filling operation can be forced out by the capillary forces at any point of the substrate and escape. This will facilitate the filling operation substantially.

Figure 9A:
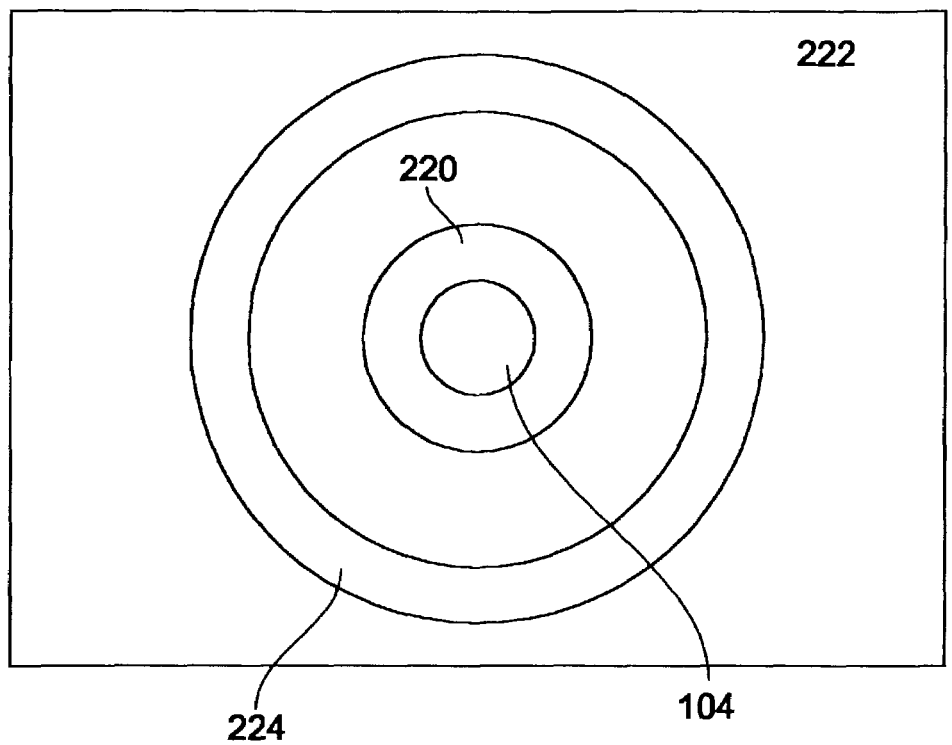
FIGS. 9A and 9B show a schematic bottom view and a schematic cross-sectional view for explaining an example of a nozzle orifice embodiment.
Figure 9B:
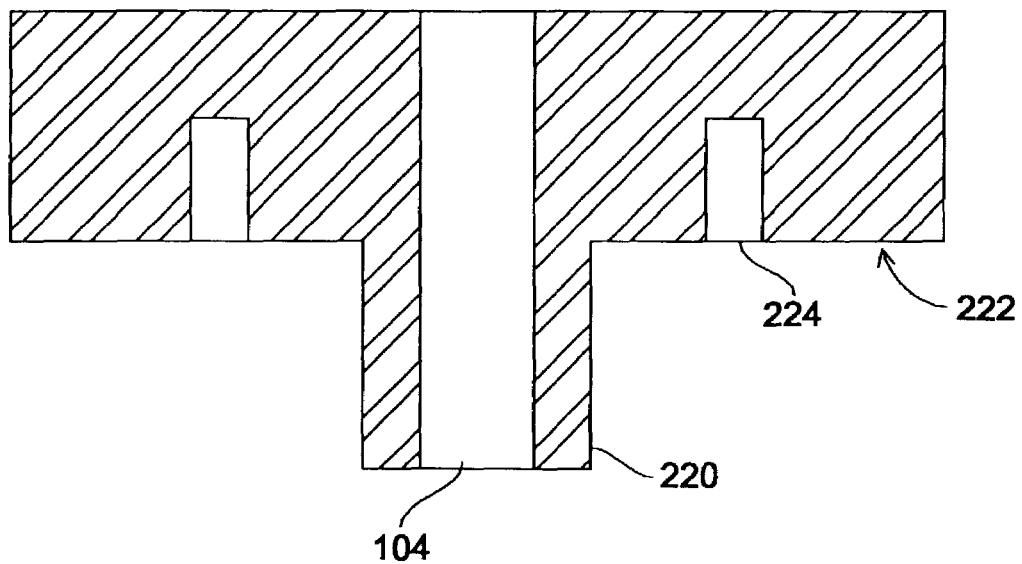

Making reference to FIGS. 9A and 9B, one embodiment which shows how the nozzles in the lower surface of the dosing-head substrate can be implemented will now be discussed in brief. FIG. 9A shows a bottom view of a possible nozzle structure, whereas FIG. 9B shows a schematic cross-sectional view thereof. A nozzle orifice 104 is surrounded by a boundary 220 which projects beyond the lower surface of the dosing-head substrate 222 in the case of the embodiment shown. As can additionally be seen from FIGS. 9A and 9B, a trench structure 224 is formed in the lower surface 222 of the dosing-head substrate; this trench structure surrounds a nozzle orifice 104 or rather the boundary 220 thereof completely. The trench structure 224 is arranged at a specific distance from the nozzle orifice 104 in such a way that, due to its structural depth, the trench 224 is capable of binding by means of capillary forces superfluous medium occurring at the nozzle orifice 104. These trenches surrounding the nozzles can also be interconnected in such a way that, by means of capillary forces, superfluous liquid will be removed from the nozzle area and transported into the outer areas of the dosing head.

Making reference to FIG. 10, the enlarged section a in FIG. 6 will now be explained in detail; FIG. 10 shows a recess 230 which is provided in the lower area of the dosing head and through which the holding device 130 can be fixed to the dosing head. FIG. 10 shows that, in the case of this embodiment, this recess, which is formed in the dosing head as a circumferentially extending recess or along certain sections thereof, is realized in that the intermediate layer 110 projects beyond the dosing-head substrate 102 and the lower cover layer 138. A supporting surface is thus formed on the lower surface 232 of the intermediate layer 110 which rests on the holding device 130 in such a way that the plane of the nozzle orifices, not shown in FIG. 10, can be positioned at the shortest possible distance from a carrier substrate which is located therebelow and onto which microdroplets are to be applied. This permits the carrier substrate to be freely moved below the dosing head at a very small distance from the nozzle orifices, but without coming into contact with these nozzle orifices. The holding device 130 can additionally be designed such that it is able to hold a plurality of dosing heads so that the respective dosing head which is to be used for carrying out the dosing operation in question can be moved below an actor simply by manipulating the holding device. In addition, the holding device can be implemented such that it may also be used as an insert device for application for the purpose of transferring media from a storage means, e.g. a titre plate, to the liquid reservoirs of the dosing heads installed in the holding device. It follows that the filling of the dosing head as well as the introduction of the full dosing head into the pressure generating means can be effected by manipulating the holding device alone.

Figure 11:
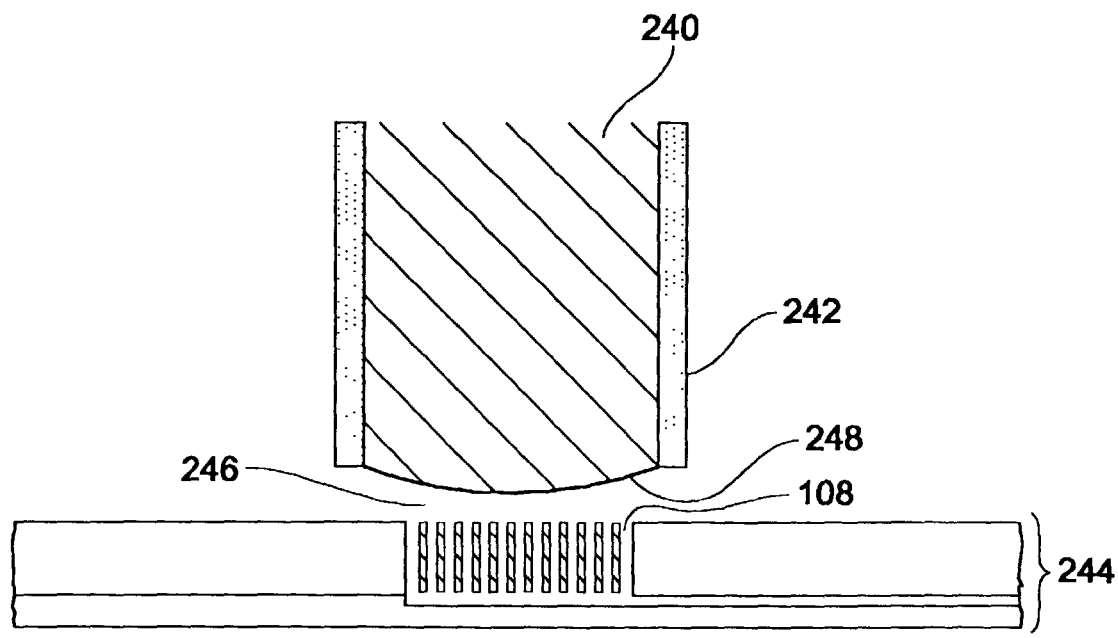
FIG. 11 shows a schematic representation of a liquid reservoir according to one embodiment of the present invention.

Biological liquids are normally transferred by means of pipetting systems from a starting format, e.g. the titre plate, to the destination. The medium to be dosed or the liquid 240 to be dosed is stored in a capillary 242. It will therefore be advantageous to provide the liquid reservoirs 108 of a dosing head with capillary intermediate bridges 246; a portion of such a dosing head is exemplarily designated by reference numeral 244 in FIG. 11. For storing liquid in the capillary 242, the capillary must be hydrophilic. When it is hydrophilic, the fluid meniscus 248 will curve outwards at the end of the capillary 242 so that the capillary intermediate bridges will destroy the surface of the stored dosing medium 240 when the pipetting capillary 242 is being attached. It is therefore not necessary that the capillary intermediate bridges project beyond the surface of the substrate of the dosing head 244. The surface tension is overcome in this way and the medium 240 is drawn into the reservoir structure 246 which produces a capillary effect. Especially in cases in which a multi-channel system is used, e.g. a needle array comprising 96 pipetting capillaries, all the reservoirs of the dosing head can be filled simultaneously by means of capillary forces in the manner described.

Figure 12:
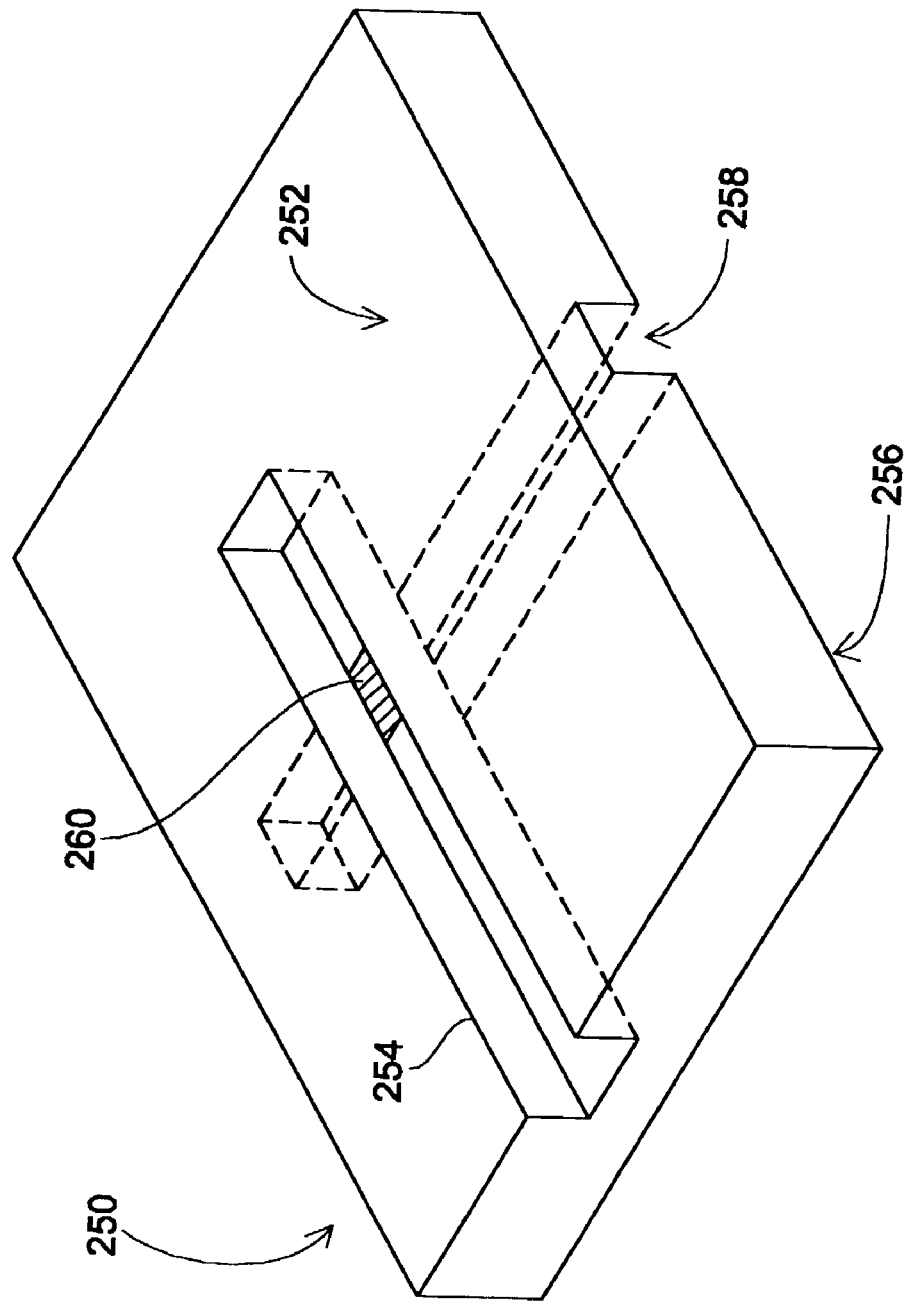
FIG. 12 shows a schematic representation for illustrating the method according to the present invention for producing a fluid opening leading from a front to a back of a fluidic substrate.

Finally, a preferred method which can be used for producing a substrate through-hole of the type provided in the above-described dosing heads of the device according to the present invention will be described making reference to FIG. 12. FIG. 12 shows schematically a section of a substrate 250 in the upper surface 252 of which a first trench 254 is produced, and in the lower surface 256 of which a second trench 258 is produced. The trenches 254 and 258 intersect at a defined angle. The depth of the trenches 254 and 258 is chosen such that, in the area of intersection, a substrate through-hole 260 is formed whose opening width is essentially defined by the width of the narrow channels 254 and 258 and by the intersection angle of the channels 254 and 258. It follows that substrate through-holes having a small, defined opening width can be produced in an advantageous manner by the method described. The advantage of such a method is to be seen in the fact that a small structure, viz. a narrow, deep channel, has to be produced in only one dimension. By producing two such channels, the sum of whose depths must be larger than the substrate thickness, a substrate through-hole 260 having an opening width which is small and defined in two dimensions will be obtained. This method of producing a small substrate through-hole has the additional advantage that the substrate through-hole will be tolerant with respect to adjustment errors of the structures on the front and on the back of the substrate. A minor misadjustment of the two structures will only cause a local displacement of the substrate through-hole, but not a change in the opening width.

The above-described method is particularly suitable for producing substrate through-holes in silicon substrates by means of conventional photolithographic patterning techniques. Alternatively, it is, however, also possible to implement substrate through-holes in substrates consisting of other materials, e.g. plastic materials, ceramics and the like, by means of arbitrary methods which are suitable for producing trenches.

Although the section of the dosing head having the nozzle orifices provided therein is formed micromechanically in a silicon substrate in the above-described preferred embodiment of the present invention, it is obvious to those skilled in the art that the dosing head, i.e. the dosing-head substrate as well as the various intermediate layers and cover layers, can be made of other suitable materials making use of suitable production techniques. The substrate can, for example, be made of a plastic material or a ceramic material making use of an injection moulding technique or an embossing technique. According to another alternative, the substrate can consist of a metal, a glass or a glass-silicon structure. The cover layers and the intermediate layers can advantageously consist of a transparent glass, e.g. a Pyrex glass.

What is claimed is:

1. A device for applying a plurality of microdroplets onto a substrate, comprising:
    a plurality of nozzle orifices in a first surface of a dosing head;
    walls for defining a liquid column of a medium to be dosed on each nozzle orifice;
    a pressure chamber which is adapted to be filled with a buffer medium and which is arranged in such a way that said buffer medium can simultaneously be used for applying a pressure to ends of the liquid-columns, which are spaced apart from the nozzle orifices;
    a pressure generator for applying a pressure to said buffer medium which in turn applies pressure to the ends of the liquid columns causing simultaneous ejection of microdroplets through the nozzle of orifices onto the substrate; and
    liquid reservoirs for the media to be dosed, which are in fluid communication with the liquid columns on the nozzle orifices and comprise reservoir openings in a second surface of said dosing head opposite to said first surface,
    wherein the reservoir openings are outside of and spaced from the pressure chamber.

2. A device according to claim 1, wherein the pressure generator is defined by a displacement diaphragm and an associated actor.

3. A device according to claim 2, wherein the buffer medium is air and wherein the pressure generator includes a compressed-air supply device which is provided with a valve and which is in fluid communication with the pressure chamber.

4. A device according to claim 1, wherein the pressure generator comprises a tappet and an actor, wherein the actor is configured to actuate the tappet to apply a pressure to the buffer medium.

5. A device according to claim 1, wherein the walls for defining a liquid column on each nozzle orifice include a channel which leads to a respective nozzle orifice and which is adapted to be filled by a capillary effect.

6. A device according to claim 1, wherein the liquid reservoirs are connected via fluid lines to the walls for defining a liquid column, said fluid lines being implemented such that they permit capillary filling of the means for defining a liquid column.

7. A device according to claim 1, comprising in addition a vent port for venting the pressure chamber.

8. A device according to claim 1, wherein the liquid reservoirs are formed in a first main surface of the dosing head, said first main surface having arranged thereon a cover plate provided with one or a plurality of vent holes for the liquid reservoirs whose cross-sectional area is smaller than that of the liquid reservoirs.

9. A device according to claim 1, comprising in addition a cooler for cooling the liquid in the liquid reservoirs.

10. A device according to claim 1, wherein the surface of the dosing head having the nozzle orifices formed therein is provided with a cover layer having an opening in the area of the nozzle orifices.

11. A device according to claim 1, wherein the dosing head is provided with recessed portions on its lateral edges in the dosing-head surface having the nozzle orifices formed therein, said recessed portions being brought into engagement with a holding device.

12. A device according to claim 11, wherein the holding device is additionally implemented as a device for applying a supply so as to fill the liquid reservoirs provided in the device.

13. A device according to claim 1, additionally comprising trench structures which surround respective nozzle orifices, said trench structures being implemented for binding by means of capillary forces superfluous liquid on the surface having the nozzle orifices formed therein.

14. A device according to claim 1, wherein the plurality of nozzle orifices and the walls for defining a liquid column are micromechanically formed in a silicon substrate.

15. A device according to claim 14, wherein also the liquid reservoirs and the fluid lines are formed, at least partially, in the silicon substrate.

16. A device according to claim 14, wherein the pressure chamber is defined by a recess formed in an intermediate plate which is applied to the silicon substrate.

17. A device according to claim 16, wherein the intermediate plate is additionally patterned so as to increase the capacity of the liquid reservoirs.

18. A device according to claim 1, wherein the liquid reservoirs are formed in the first surface of the dosing head, said liquid reservoirs having arranged therein capillary structures.

19. A device according to claim 1, wherein the ends of the liquid-columns, which are spaced apart from the nozzle orifices, are fluid insulated from each other by the buffer medium.

* * * * *